United States Patent
Bindra et al.

(10) Patent No.: US 9,421,085 B2
(45) Date of Patent: Aug. 23, 2016

(54) SURGICAL METHODS FOR SOFT TISSUE REPAIR

(75) Inventors: Randip R. Bindra, Clarendon Hills, IL (US); Dale R. Peterson, La Jolla, CA (US); Kevin L. Ohashi, Jamaica Plain, MA (US)

(73) Assignee: Tornier, Inc., Bloomington, MN (US)

( * ) Notice: Subject to any disclaimer, the term of this patent is extended or adjusted under 35 U.S.C. 154(b) by 545 days.

(21) Appl. No.: 13/221,766

(22) Filed: Aug. 30, 2011

(65) Prior Publication Data

US 2012/0226296 A1    Sep. 6, 2012

Related U.S. Application Data

(60) Provisional application No. 61/379,298, filed on Sep. 1, 2010.

(30) Foreign Application Priority Data

Sep. 3, 2010 (EP) .................. 10305953

(51) Int. Cl.
*A61F 2/08* (2006.01)
*A61B 17/11* (2006.01)

(52) U.S. Cl.
CPC ............. *A61F 2/08* (2013.01); *A61B 17/1146* (2013.01); *A61F 2/0811* (2013.01); *A61F 2002/0894* (2013.01)

(58) Field of Classification Search
CPC .............. A61B 17/11; A61B 17/1146; A61B 2017/1132; A61B 17/0466; A61F 2/0811; A61F 2/0805; A61F 2/08
USPC ........... 606/151, 152, 153; 623/13.13, 13.15, 623/13.11, 13.16
See application file for complete search history.

(56) References Cited

U.S. PATENT DOCUMENTS 4,662,884 A * 5/1987 Stensaas et al. .............. 606/152
5,486,187 A * 1/1996 Schenck ....................... 606/151
(Continued)

FOREIGN PATENT DOCUMENTS

| WO | 0156506 A1 | 8/2001 |
|---|---|---|
| WO | 2005122954 A1 | 12/2005 |
| WO | 0167944 A2 | 9/2011 |

OTHER PUBLICATIONS

European Search Report issued in Application No. 10305953.1, mailed Feb. 14, 2011, 7 pages.
(Continued)

*Primary Examiner* — Brian Pellegrino
(74) *Attorney, Agent, or Firm* — Knobbe, Martens, Olson & Bear, LLP

(57) ABSTRACT

The device (1) comprises a first snare (10) and a second snare (20), each of these snares comprising a contractable hollow elongated body (11, 21) which defines a longitudinal central axis (X10, X20) and which reduces its cross section when two opposed first (12, 22) and second (13, 23) ends thereof are axially moved away from each other. The first end (12) of the first snare (10) and the first end (22) of the second snare (20) are each open and adapted to be fitted and tightened around, respectively, two stumps (T1, T2) of a soft tissue (T) to be repaired. The second end (13) of the first snare (10) and the second end (23) of the second snare (20) are adapted to the axially pulled so that the second end of each of the two snares is passed alongside or through the body (11, 21) of the other snare.

19 Claims, 3 Drawing Sheets

(56) References Cited

U.S. PATENT DOCUMENTS

| | | | | |
|---|---|---|---|---|
| 5,800,544 | A | * | 9/1998 | Demopulos ........ A61B 17/1146 606/53 |
| 5,897,591 | A | * | 4/1999 | Kobayashi ................. 606/151 |
| 6,214,047 | B1 | * | 4/2001 | Melvin ..................... 623/13.11 |
| 6,342,060 | B1 | * | 1/2002 | Adams ..................... 623/13.15 |
| 2009/0054928 | A1 | | 2/2009 | Denham et al. |

OTHER PUBLICATIONS

Paul, D.R. et al., "*Cellulosic Polymers*", Polymer Blends, 1978, vol. 2, pp. 378-379.

* cited by examiner

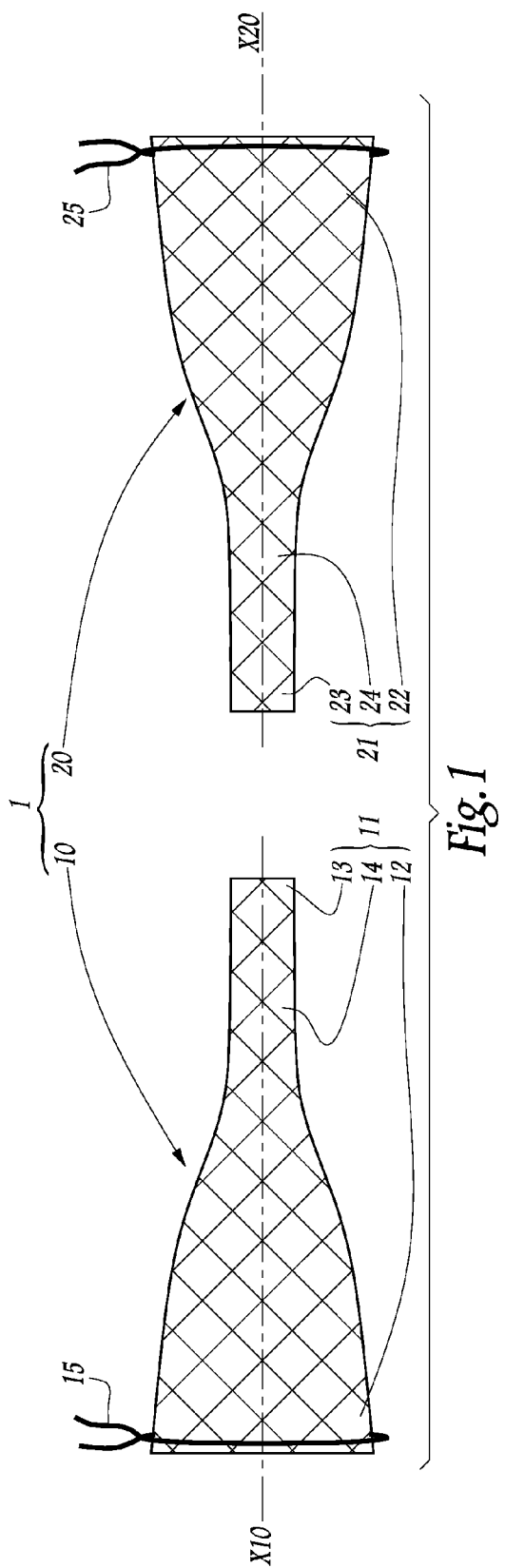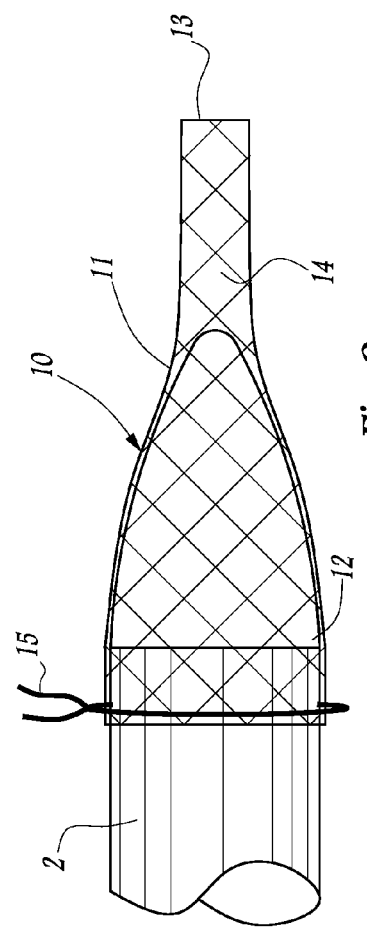

SURGICAL METHODS FOR SOFT TISSUE REPAIR

CROSS-REFERENCE TO RELATED APPLICATIONS

This application claims the benefit of U.S. Provisional Patent Application Ser. No. 61/379,298, filed on Sep. 1, 2010, and claims foreign priority to European Patent Application No. 10305953.1, filed on Sep. 3, 2010, both of which are incorporated by reference herein in their entireties for all purposes.

TECHNICAL FIELD

The present invention relates to a surgical device for soft tissue repair, especially for tendon repair. The invention relates also to a surgical kit for soft tissue repair, including such a device.

BACKGROUND

Generally, when a damaged tendon is surgically repaired, the two opposed remaining stumps of the tendon are held by the surgeon using clamps or hemostats, then are tied together by sutures after putting locking stitches in place in each stump. This standard technique is widely criticized because the excessive handling of the tendon stumps may lead to further fraying and weakening of the tendon and may increase the risk of adhesions, and because there is typically some slack in the knots holding the two stumps together, which leads to a gap.

Due to the fact that the ends of a tendon to be repaired are frayed, there is a significant difficulty to conceive an efficient device for assisting a surgeon in tendon repair, which explains why the aforesaid surgical standard technique has been performed for decades. However, this standard technique often corresponds to an unsatisfactory compromise between preservation of the frayed tissues and control of the diameter of the repaired tendon.

SUMMARY

Embodiments of the present invention repair a human torn or ruptured soft tissue, particularly a tendon. A device for repairing a soft tissue according to embodiments of the present invention may be efficient and easy to use.

To this end, a surgical device for soft tissue repair is recited in appended claim 1. Additional features of this device are specified in dependent claims 2 to 14. A surgical kit for soft tissue repair is recited in appended claim 15.

Furthermore, a surgical method for repairing a soft tissue according to embodiments of the present invention may include:
 providing a first snare and a second snare, each of these first and second snares comprising a contractable hollow elongated body which defines a longitudinal central axis and which is adapted to reduce its cross section when two opposed first and second ends thereof are axially moved away from each other,
 fitting and tightening the first end of the first snare and the first end of the second snare around, respectively, two stumps of a soft tissue to be repaired,
 pulling the second end of each of the first and second snares opposite the first end thereof to move closer the stumps of the soft tissue to each other, the second end of each of the two snares being passed alongside or through the body of the other snare.

According to embodiments of the present invention, two snares are combined or otherwise attached to one another in new ways. When a surgeon uses the device according to embodiments of the invention for performing the above defined method, the surgeon can approximate the soft tissue stumps and sew them with a single series of locking stitches without the need to tie the two stumps together afterwards, which reduces gap formation. Also, the two contractable bodies of the device according to embodiments of the invention are respectively able to capture the frayed ends of the soft tissue and to hold them in a small controlled volume, which simplifies and improves suturing. Furthermore, the device according to embodiments of the invention reduces damage to the soft tissue stumps from handling during the suturing. After the sutures are complete, the tension on the two snares of the device may be released and their respective parts, which are not tightened around the soft tissue and which form tails, may be trimmed away.

A surgical method for repairing a soft tissue, the soft tissue having a first stump and a second stump, according to embodiments of the present invention includes inserting a first end of a first snare over the first stump, the first snare comprising a contractable hollow elongated body which is adapted to reduce its cross section when tensioned longitudinally; inserting a first end of a second snare over the second stump, the second snare comprising a contractable hollow elongated body which is adapted to reduce its cross section when tensioned longitudinally; tightening the first end of the first snare onto the first stump; tightening the first end of the second snare onto the second stump; pulling a second end of the first snare toward a second end of the second snare; and joining the first snare to the second snare. The first snare may be identical to the second snare. Joining the first snare to the second snare may include inserting the second end of one of the first and second snares through the other of the first and second snares. The first and second snare may be braided, and inserting the second end of the one of the first and second snares through the other of the first and second snares may include inserting the second end of the one of the first and second snares between braided filaments of the other of the first and second snares.

According to such embodiments of methods, joining the first snare to the second snare may include stitching the first and second snares together. Joining the first snare to the second snare may include pulling the first snare alongside the second snare before stitching the first and second snares together. Joining the first snare to the second snare may include clamping the first and second snares together. Such methods may further include radially contracting the first end of the first snare by pulling the first snare in a direction away from the first stump. The first stump may include a plurality of frayed tendrils, and the first snare may have a wider opening at the first end than at the second end, and inserting the first end of the first suture over the first stump may include inserting the wider opening at the first end over the plurality of frayed tendrils. The first snare may include a first tightening mechanism at the first end, and tightening the first end of the first snare onto the first stump may include activating the tightening mechanism. The tightening mechanism may be a draw string, and activating the tightening mechanism may include pulling one or more free ends of the draw string. Such methods may further include loosening the tightening mechanism, for example after the first snare has been joined to the second snare. Such methods may also include suturing the first stump to the second stump using the same suture and without tying a knot between the first and second stumps. The first stump may be sutured to the second stump using Kessler stitch pattern. Such methods may further include trimming away excess portions of the first and second snares from their second ends.

The first snare and the second snares may be formed from a snare tube, each end of the snare tube corresponding to the first ends of the first and second snares, and such methods may further include cutting the snare tube to separate the first snare from the second snare, such that the location of the cutting corresponds to the second ends of the first and second snares. The soft tissue repaired may be, for example, a human hand flexor tendon.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 1 is a schematic elevation view of a device according to an embodiment of the present invention;

FIG. 2 is a schematic elevation of one of the two snares of the device of FIG. 1, during the fabrication thereof.

Figure 3:
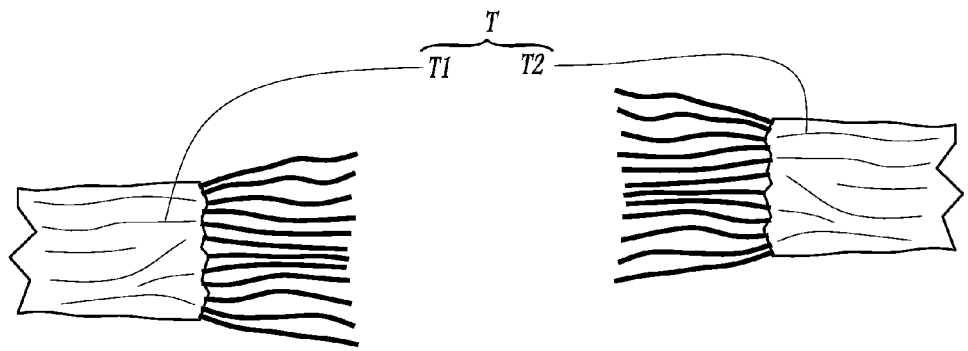
FIGS. 3 to 8 are schematic elevation views showing steps of repair of a tendon by the device of FIG. 1, according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 depicts a device 1 for repairing a tendon. Device 1 comprises two distinct snares 10 and 20. In the shown embodiment, these two snares 10 and 20 are identical.

Each of the snares 10 and 20 comprises a main hollow elongated body 11, 21 extending in length about a central axis X10, X20 between two opposed ends 12 and 13, 22 and 23 of the body, which are substantially centered on axis X10, X20.

According to one embodiment, each body 11, 12 is constituted by a tubular braid helically wound around axis X10, X20. This wound braid is fabricated so that pulling axially the entire braid lengthens and narrows it. In particular, according to one embodiment, the aforesaid braid is a biaxial braid: the length of body 11, 21 can be increased by reducing the angle between the two braiding directions of the braid, which reduces the cross section of the body. This braiding structure of body 11, 21 implies that the more the entire braid is pulled, the more the cross sectional area and/or perimeter of the body shrinks.

According to one embodiment, the braid of body 11, 21 is made of a resorbable and biocompatible polymer. In particular, the braided filaments may be made of polyhydroxyalkanoate, for example of TephaFlex (registered mark) which corresponds to poly-4-hydroxybutyrate. Another possible choice for an appropriate polymer is polydioxanone (PDS). Alternatively, nonpolymeric fibers can be used, for example wire, or biologic tissues such as catgut, silk, tendon, or natural polymers like collagen, elastin, keratin, proteoglycans. According to another embodiment, nonresorsable materials are used for bodies 11 and 12.

In one embodiment, the filaments of the braid of body 11, 21 are monofilaments. Such monofilaments maintain space or pores between their intersections which encourages soft tissue growth into body 11, 21. According to a non limiting example, the diameter of these monofilaments is between 30 and 500 µm, and the number of these braided monofilaments in the braid of each body 11, 21 is between 4 and 12. In other words, body 11, 21 may be constituted by a very light braid. According to another embodiment, a sparse braid of multifilament yarns is used, though the resulting snare may not hold its shape or collapse in diameter as readily as one fabricated with a monofilament braid. According to another embodiment (not shown), the snares 10 and 20 are woven.

In the embodiment shown in FIG. 1, body 11, 21 is not cylindrical: its open end 12, 22 is flared. In other words, the end 12, 22 includes a diameter that increases along axis X10, X20 opposite end 13, 23, up to a maximal value at the free open part of this end 12, 22, which may be at least twice as large as the diameter of the rest of body 11, 21. As an example, the diameter of the intermediate longitudinal part 14, 24 of body 11, 21, extending between the opposed ends 12 and 13, 22 and 23, may be about 1 mm. The flared end shape of body 11, 21 is discussed further, below.

In practice, flared end 12, 22 of body 11, 21 axially protrudes from intermediate part 14, 24 of the body without angulation. According to one embodiment, this flared end has a bell shape centered on axis X10, X20.

In order to fabricate each snare 10, 20, a mandrel 2 may be used, as represented in FIG. 2. More precisely, the filaments constituting body 11, 21 of snare 10, 20 may be braided over this mandrel 2 in order to fabricate the braid and to form this braid in a tubular shape, particularly in the aforesaid bell shape. In particular, as represented in FIG. 2, the mandrel may have an ogival or tapered external face around which flared end 12, 22 of body 11, 21 is braided and thus conformed. Optionally, the braid constituting body 11, 21 is heat-set on mandrel 2 in order to stabilize the flared shape of its end 12, 22.

Mandrel 2 may be used to achieve a flared shape of end 12, 22 of body 11, 21 when the braid constituting this body is doubled back upon itself, according to embodiments of the present invention. More precisely, during braiding, the mandrel is fed into the core of the braid until it is covered by the braid filaments for the desired distance and then it is slowly withdrawn from the core so that end is covered with another layer of braiding. In other words, each braid constituting the bodies 11 and 21 is folded back like a sock. In this way, the folded portion of these filaments, where the braid is bended or folded upon itself, forms end 12, 22 of body 11, 21, while all the loose ends of the filaments are located at end 13, 23 of the body, according to embodiments of the present invention. Thus, end 12, 22 of body 11, 21 is stable and collapsible, in the sense that this end cannot be easily unravelled. In order to limit the risk of unravelling at end 13, 23 of body 11, 21, intermediate part 14, 24 of this body may be provided with a significant length and/or end 13, 23 may be tightly braided like a tail.

In the embodiment shown in FIG. 1, flared end 12, 22 of body 11, 21 is may be provided with a drawstring 15, 25 which surrounds the free part of this flared end. In practice, this drawstring 15, 25 slidably interlaces the filaments constituting flared end 12, 22 so that, when this drawstring is pulled on, the drawstring tightens the flared end and radially reduces the cross section thereof. In this way, flared end 12, 22 of body 11, 21 is able to be tightened on itself independently from contraction of body 11, 21 when the ends 12 and 13, 22 and 23 thereof are axially moved away from each other.

In practice, drawstring 15, 25 is a non limiting example of a tightening mechanism. Another example of such a tightening mechanism includes a yarn encircling the flared end 12, 22 of body 11, 21, this yarn being provided with, at the opposed ends thereof, a closed loop and a swaged needle to be threaded through the aforesaid closed loop. Although one particular example of the shape of the bodies 11 and 21 is illustrated, other jointed or sophisticated cut-out shapes may be used.

An example of the use of device 1 will be now explained in reference to FIGS. 3 to 8. FIG. 3 depicts a ruptured tendon T. In the damaged state shown in FIG. 3, two stumps T1 and T2 of the tendon are facing each other, being separated by a free gap. As typically observed in this context, the free end of each tendon stump T1, T2 is frayed and corresponds to a plurality of tendrils.

Device 1 may be used to assist in repairing tendon T. In practice, this repair is performed by a surgeon who has at his disposal device 1 in a rest configuration, which corresponds to the configuration thereof shown in FIG. 1.

Figure 4:
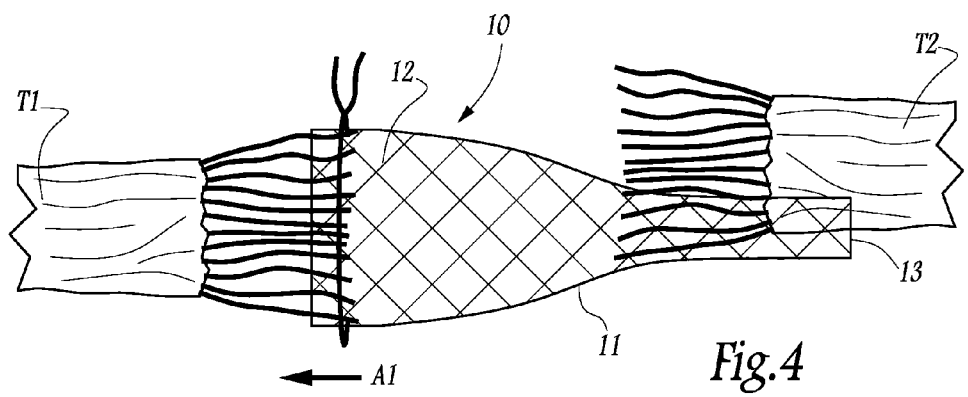

In a first step shown in FIG. 4, snare 10 of device 1 is fitted around tendon stump T1, by being slid over this stump, as indicated by an arrow A1. More precisely, tendon stump T1 is axially introduced within flared end 12 of body 11. This fitting is facilitated by the flared shape of this end 12, which facilitates capturing all the frayed tendrils of the stump within the body.

Figure 5:
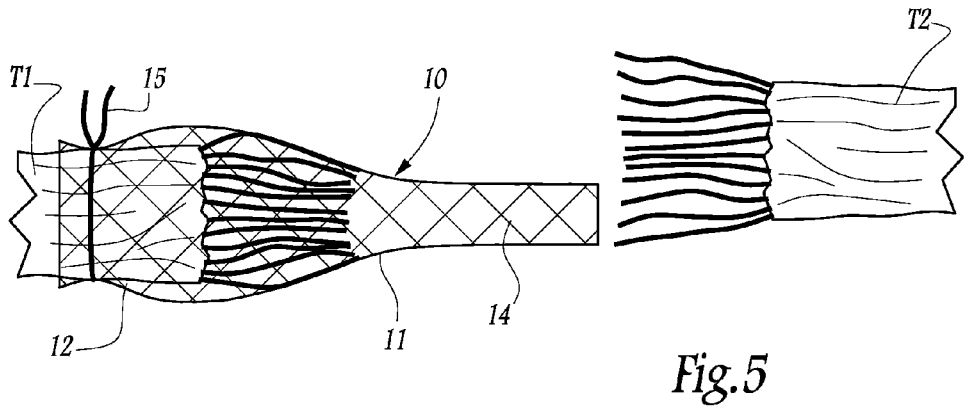

In a second step shown in FIG. 5, flared end 12 of body 11 is tightened around tendon stump T1, by an action on drawstring 15. In practice, this tightening is performed at any desired location along the stump. In this configuration, opposed end 13 of body 11 is axially beyond the free end of tendon stump T1, due to a sufficient length of intermediate part 14 of the body.

Figure 6:
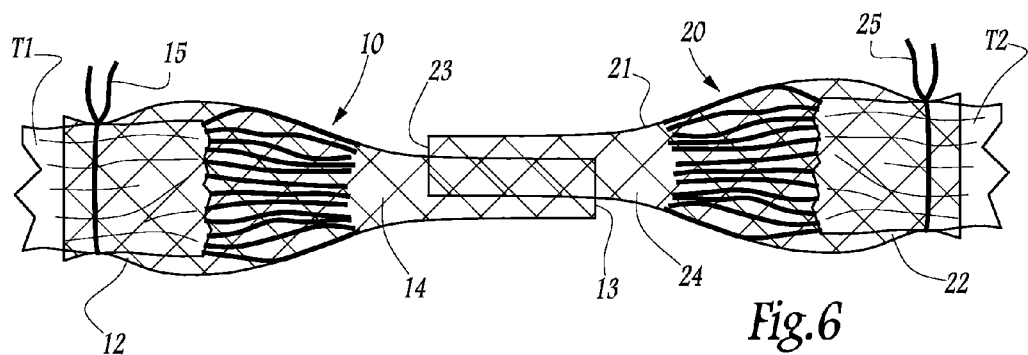

In a third step shown in FIG. 6, snare 20 of device 1 is fitted and tightened around tendon stump T2 in the same way as snare 10 was fitted and tightened around stump T1.

Figure 7:
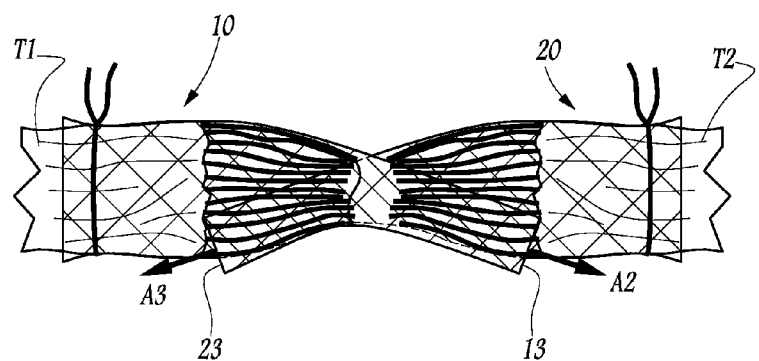

In a fourth step shown in FIG. 7, the ends 13 and 23 of the snares 10 and 20 are passed alongside and/or through each other. According to one embodiment of the present invention, the snares 10 and 20 are tightened by pulling axially on each end 13, 23 independently before or after threading either one or each of these ends 13 and 23 through the other snare by passing between the braided filaments thereof. Thus, end 13 of body 11 is axially pulled opposite end 12 of this body and, at the same time, end 23 of body 21 is pulled opposite end 22, as indicated by arrows A2 and A3: each of these two pulling motions axially separates the two ends of each of bodies 11 and 21, which induces the radial contraction of these bodies around, respectively, stump T1 and stump T2. During the contraction of bodies 11 and 21, the cross sections thereof progressively reduce, both at their flared ends 12 and 22 and along their intermediate parts 14 and 24. By that way, the stumps T1 and T2 are tightly grasped by the snares 10 and 20, for example by the flared ends 12 and 22 and by adjacent portions of the intermediate parts 14 and 24. Thus, the frayed ends of the tendon stumps T1 and T2 are held in a small controlled volume centered on the axes X10 and X20 which are substantially aligned. The damaged tendon stumps T1 and T2 are thus reduced, according to embodiments of the present invention.

Besides, the pulling actions on the ends 13 and 23 force the tendon stumps T1 and T2 to move closer to each other, which reduces the free gap between them. As at least end 13 or 23 of one of the snares 10 and 20 passes through the side of the other snare, the tendon stumps are in intimate contact with each other and are substantially aligned. In practice, the surgeon controls the relative bringing of the two tendon stumps T1 and T2 together by applying appropriate axial tensions on bodies 11 and 21, respectively, corresponding to appropriate pulling actions on the ends 13 and 23 of the snares 10 and 20.

Alternatively, rather than threading one or each of the ends 13 and 23 through the other snare 20 or 10 after having pulled on them, the ends 13 and 23 may extend alongside each other and be sutured directly onto each other. In this case, more generally, after having pulled these ends 13 and 23 alongside each other and placing them side by side, they may be secured to each other by any added appropriate device which is put in place by the surgeon.

Figure 8:
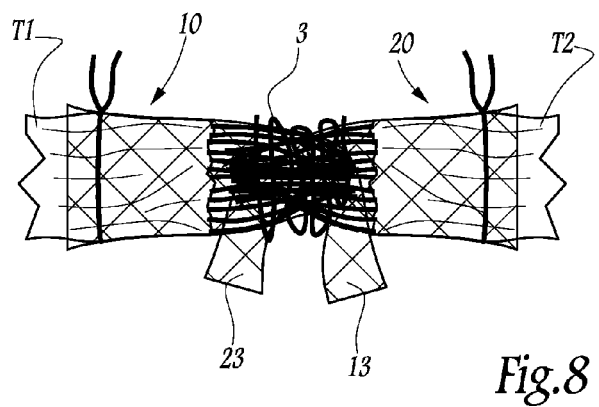

In a fifth step shown in FIG. 8, while the snares 10 and 20 are maintained under tension by an operator or by at least one element for securing the snares to each other, such as a suture or a clip, the surgeon uses sutures 3 to suture together the two tendon stumps T1 and T2. In practice, the surgeon passes the sutures 3 through the bodies 11 and 21 of the snares 10 and 20 and into the tendon stumps. This suturing of the tendon stumps T1 and T2 may be performed in a standard manner, while the snares 10 and 20 keep the tendon in place. As the free ends of the stumps T1 and T2 are close to each other, the same suture may be run through the two stumps T1 and T2 without the need to tie any knot between the two stumps. Thus, this suturing is simplified and healing of the repaired tendon T is improved. The stitch pattern drawn in FIG. 8 is only diagrammatic. In practice, known stitch patterns may be used, such as the Kessler stitch pattern. Of course, another device may be used to hold the stumps together, in addition to or in replacement of the sutures 3. Once the tendon stumps T1 and T2 are sutured together, tension on the snares 10 and 20 may be relaxed at least in part so that the repaired tendon T is not strangulated permanently. Also, the ends 13 and 23 of the snares 10 and 20, and respective adjacent portions of their intermediate parts 14 and 24, may be trimmed away. Alternatively, the fifth step may be omitted when the snares 10 and 20 are sufficiently secured to each other for reducing and holding the stumps together. After implantation, the snares 10 and 20 or their remaining parts may be left in place and may be resorbed.

Although the attachment method of FIGS. 3-8 includes steps described as being performed in a certain order, one of ordinary skill in the art will appreciate that the steps may be performed in differing orders, and that some steps may be omitted and others added, according to embodiments of the present invention.

According to another embodiment of the present invention (not shown), rather than having at his disposal the two snares 10 and 20 separate from each other at the beginning of the surgery, the surgeon may have a single tubular member, for example a tubular member with two flared opposed ends. Then, the surgeon may cut this member in half at various steps in the surgery, for example before packaging for a future use, or upon opening in the operating room, or after capturing both stumps, or even after tightening on one of the two stumps.

As one non-limiting example, device 1 may be ideal for hand flexor tendon repairs because the snares 10 and 20 reduce the bulk of the repair so the tendon can pass freely through the sheath and pulleys.

More generally, the device according to embodiments of the invention may be used for repairing other soft tissue, especially to help reduce defects or difficult to reach structure.

Other variations are possible according to other embodiments of the present invention, including by recombining the various elements disclosed herein in different or alternative combinations. Although the above description contains many specifics, this should not be considered as limiting the scope of the invention as defined by the appended claims, but as merely providing illustrations of some of the embodiments of this invention.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A surgical method for repairing a soft tissue, the soft tissue having a first stump and a second stump, the method comprising:
    inserting a first end of a first snare over the first stump, the first snare comprising a contractable hollow elongated body which is adapted to reduce its cross section when tensioned longitudinally;
    inserting a first end of a second snare over the second stump, the second snare comprising a contractable hollow elongated body which is adapted to reduce its cross section when tensioned longitudinally;
    tightening the first end of the first snare onto the first stump;
    tightening the first end of the second snare onto the second stump;
    pulling a second end of the first snare toward a second end of the second snare; and
    joining the first snare to the second snare, wherein joining the first snare to the second snare comprises inserting the second end of one of the first and second snares through the other of the first and second snares.

2. The surgical method of claim 1, wherein the first snare is identical to the second snare.

3. The surgical method of claim 1, wherein the first and second snare are braided, and wherein inserting the second end of the one of the first and second snares through the other of the first and second snares comprises inserting the second end of the one of the first and second snares between braided filaments of the other of the first and second snares.

4. The surgical method of claim 1, wherein joining the first snare to the second snare comprises stitching the first and second snares together.

5. The surgical method of claim 1, wherein joining the first snare to the second snare comprises clamping the first and second snares together.

6. The surgical method of claim 1, further comprising radially contracting the first end of the first snare by pulling the first snare in a direction away from the first stump.

7. The surgical method of claim 1, wherein the first stump comprises a plurality of frayed tendrils, wherein the first snare has a wider opening at the first end than at the second end, wherein inserting the first end of the first snare over the first stump comprises inserting the wider opening at the first end over the plurality of frayed tendrils.

8. The surgical method of claim 1, wherein the first snare comprises a first tightening mechanism at the first end, and wherein tightening the first end of the first snare onto the first stump comprises activating the tightening mechanism.

9. The surgical method of claim 8, wherein the tightening mechanism is a draw string, and wherein activating the tightening mechanism comprises pulling one or more free ends of the draw string.

10. The surgical method of claim 8, further comprising loosening the tightening mechanism.

11. The surgical method of claim 8, further comprising loosening the tightening mechanism after the first snare has been joined to the second snare.

12. The surgical method of claim 1, further comprising suturing the first stump to the second stump with a suture through the first stump and the second stump and without tying a knot between the first and second stumps.

13. The surgical method of claim 1, further comprising suturing the first stump to the second stump using a Kessler stitch pattern.

14. The surgical method of claim 1, further comprising trimming away excess portions of the first and second snares from their second ends.

15. The surgical method of claim 1, wherein the first snare and the second snares are formed from a snare tube, each end of the snare tube corresponding to the first ends of the first and second snares, the method further comprising cutting the snare tube to separate the first snare from the second snare, wherein the location of the cutting corresponds to the second ends of the first and second snares.

16. The surgical method of claim 1, wherein the soft tissue is a human hand flexor tendon.

17. A surgical method for repairing a soft tissue, the soft tissue having a first stump and a second stump, the method comprising:
    inserting a first end of a first snare over the first stump, the first snare comprising a contractable hollow elongated body which is adapted to reduce its cross section when tensioned longitudinally,
    inserting a first end of a second snare over the second stump, the second snare comprising a contractable hollow elongated body which is adapted to reduce its cross section when tensioned longitudinally,
    tightening the first end of the first snare onto the first stump;
    tightening the first end of the second snare onto the second stump;
    pulling a second end of the first snare toward a second end of the second snare;
    joining the first snare to the second snare; and
    after joining the first snare to the second snare, advancing a suture into the first stump and into the second stump to join the stumps together.

18. The surgical method of claim 17, wherein joining the first snare to the second snare comprises pulling the first snare alongside the second snare before stitching the first and second snares together.

19. The surgical method of claim 17, further comprising, after advancing the suture into the first stump and into the second stump, relaxing the tension at least in part in at least one of the first snare and the second snare.

* * * * *